US006941599B2

(12) United States Patent
Zacharopoulos et al.

(10) Patent No.: US 6,941,599 B2
(45) Date of Patent: Sep. 13, 2005

(54) RADIOTHERAPY TREATMENT AND IMAGING PATIENT SUPPORT TABLE

(75) Inventors: Nick Zacharopoulos, New City, NY (US); Matthew Recchia, Port Chester, NY (US)

(73) Assignee: Aktina Medical Corp., Congers, NY (US)

( * ) Notice: Subject to any disclaimer, the term of this patent is extended or adjusted under 35 U.S.C. 154(b) by 0 days.

(21) Appl. No.: 10/866,293

(22) Filed: Jun. 12, 2004

(65) Prior Publication Data

US 2005/0005356 A1 Jan. 13, 2005

Related U.S. Application Data

(63) Continuation-in-part of application No. 10/223,912, filed on Aug. 20, 2002.

(51) Int. Cl.[7] .............................................. A61G 13/00
(52) U.S. Cl. ............................... 5/601; 5/613; 378/209
(58) Field of Search ...................... 5/601, 613; 378/209

(56) References Cited

U.S. PATENT DOCUMENTS

| | | | | |
|---|---|---|---|---|
| 2,872,259 A | * | 2/1959 | Thorpe | ........................ 5/613 |
| 3,700,229 A | | 10/1972 | Kurokawa et al. | |
| 3,814,419 A | | 6/1974 | Bjorklund et al. | |
| 3,840,221 A | | 10/1974 | Hogan | |
| 3,845,947 A | * | 11/1974 | Lee | ............................. 5/613 |
| 3,868,103 A | * | 2/1975 | Pageot et al. | .................. 5/614 |
| 3,981,492 A | | 9/1976 | Hallmann | |
| 4,143,652 A | | 3/1979 | Meier et al. | |
| 4,212,454 A | * | 7/1980 | Lee | ............................. 5/613 |
| 4,487,523 A | | 12/1984 | Monroe | |
| 4,520,800 A | | 6/1985 | Kowalski | |
| 4,901,964 A | | 2/1990 | McConnell | |
| 5,385,119 A | | 1/1995 | Tarulli | |
| 5,400,772 A | | 3/1995 | LeVahn et al. | |
| 5,452,721 A | | 9/1995 | Hacker | |
| 5,531,229 A | | 7/1996 | Dean et al. | |
| 5,537,454 A | | 7/1996 | Korver, II | |
| 5,566,681 A | | 10/1996 | Manwaring et al. | |
| 5,689,545 A | | 11/1997 | Hopkins | |
| 5,754,997 A | * | 5/1998 | Lussi et al. | .................... 5/601 |
| 5,775,337 A | | 7/1998 | Hauger et al. | |
| 5,806,116 A | | 9/1998 | Oliver et al. | |
| 5,832,550 A | | 11/1998 | Hauger et al. | |
| 5,848,449 A | | 12/1998 | Hauger et al. | |
| 5,983,426 A | | 11/1999 | Vanek et al. | |
| 6,152,599 A | | 11/2000 | Salter, Jr. | |
| 6,161,237 A | | 12/2000 | Tang et al. | |
| 6,279,579 B1 | | 8/2001 | Riaziat et al. | |
| 6,298,506 B1 | * | 10/2001 | Heinold et al. | ................. 5/601 |
| 6,341,398 B1 | | 1/2002 | Heimbrock et al. | |
| 6,408,464 B1 | * | 6/2002 | Weismiller et al. | ............ 5/602 |

(Continued)

Primary Examiner—Frederick L. Lagman
(74) Attorney, Agent, or Firm—Jones Day (57) ABSTRACT

An improved patient support table including a first or fixed table section and a second or removable table section to allow the second table section to be exchanged with other second table sections of different structure. Each of the table sections includes a mating connector end portion where two pairs of horizontally disposed pads on the fixed table section engage two pairs of horizontally disposed pads on the removable table section, where a curved edge of the removable table section engages a vertical edge on the fixed table section, and where vertical side walls of the fixed table section are engaged by beveled pegs on the removable table section. The pads, edges, walls and pegs align and support the removable table section relative to the fixed table section in the x, y, z directions, the traditional, three dimensional, mutually perpendicular coordinate system. The table sections also include cam pivoting mechanisms, each having a block, a spring biased pivotal arm having a circular recess and a rod for engaging the circular recess of the arm and creating an interference fit.

40 Claims, 8 Drawing Sheets

U.S. PATENT DOCUMENTS

| | | |
|---|---|---|
| 6,493,571 B1 | 12/2002 | Bis et al. |
| 6,499,158 B1 | 12/2002 | Easterling |
| 6,671,904 B2 | 1/2004 | Easterling |
| 2004/0034932 A1 * | 2/2004 | Zacharopoulos et al. ...... 5/601 |
| 2005/0028279 A1 * | 2/2005 | de Mooy ...................... 5/601 |

* cited by examiner

RADIOTHERAPY TREATMENT AND IMAGING PATIENT SUPPORT TABLE

CROSS REFERENCE TO RELATED APPLICATIONS

The present invention is a continuation-in-part of application Ser. No. 10/223,912, entitled PATIENT SUPPORT SYSTEM AND ELEMENTS THEREOF, filed on Aug. 20, 2002 and priority is claimed for all common subject matter.

STATEMENT REGARDING FEDERALLY SPONSORED RESEARCH

Not applicable.

BACKGROUND OF THE INVENTION

1. Field of the Invention

The present invention relates to an improved patient support table and, more particularly, to an improved connector system for the support table. The table is divided into two sections where one section is exchangeable with other sections of different designs. This adds versatility to enhance treatment and imaging.

2. Description of the Related Art

Patient support tables are used in the medical field in radiation therapy and CT scanning and for other medical procedures. The uses and concerns regarding patient support tables are explained in the above mentioned parent patent application and are incorporated here by this reference.

The exchangeable feature of these tables require that the exchangeable or movable table sections be easily and repeatedly connected to a table section that is relatively fixed and is also explained in the parent application. The pair of connector latch mechanisms disclosed in the parent application has proven to be somewhat cumbersome and operators at times forget to latch both sides of the table. Thus, there developed a desire to improve the connector system. This has been done and is described here.

BRIEF SUMMARY OF THE INVENTION

The improved radiotherapy treatment and imaging patient support table disclosed here offers a number of beneficial features. What is discribed is a radiotherapy treatment and imaging patient support table including a first table section, a second table section, the second table section being removably attachable to the first table section, and a connector system having three sets of separated structural surfaces, a first portion of each set formed on the first table section and a second portion of each set formed on the second table section.

There are a number of advantages, features and objects achieved with the present invention which are believed not to be available in earlier related devices. For example, two advantages are that the present invention provides a patient support table that is simply operated and easy to use resulting in a more foolproof operation. Other features are that the support table is robust, reliable and uncomplicated. Still another object of the present invention is that the support table described herein provides for accurate and repeatable alignment of the exchangeable sections of the table. In addition, the support table includes an energy absorbing feature if accidentally bumped during use or setup.

A more complete understanding of the present invention and other objects, advantages and features thereof will be gained from a consideration of the following description of a preferred embodiment read in conjunction with the accompanying drawing provided herein. The preferred embodiment represents an example of the invention which is described here in compliance with Title 35 U.S.C. section 112 (first paragraph), but the invention itself is defined by the attached claims.

DETAILED DESCRIPTION OF A PREFERRED EMBODIMENT OF THE INVENTION

While the present invention is open to various modifications and alternative constructions, the preferred embodiment shown in the various figures of the drawing will be described herein in detail. It is understood, however, that there is no intention to limit the invention to the particular embodiment, form or example disclosed. On the contrary, the intention is to cover all modifications, equivalent structures and methods, and alternative constructions falling within the spirit and scope of the invention as expressed in the appended claims, pursuant to Title 35 U.S.C. section 112 (second paragraph).

Figure 1:
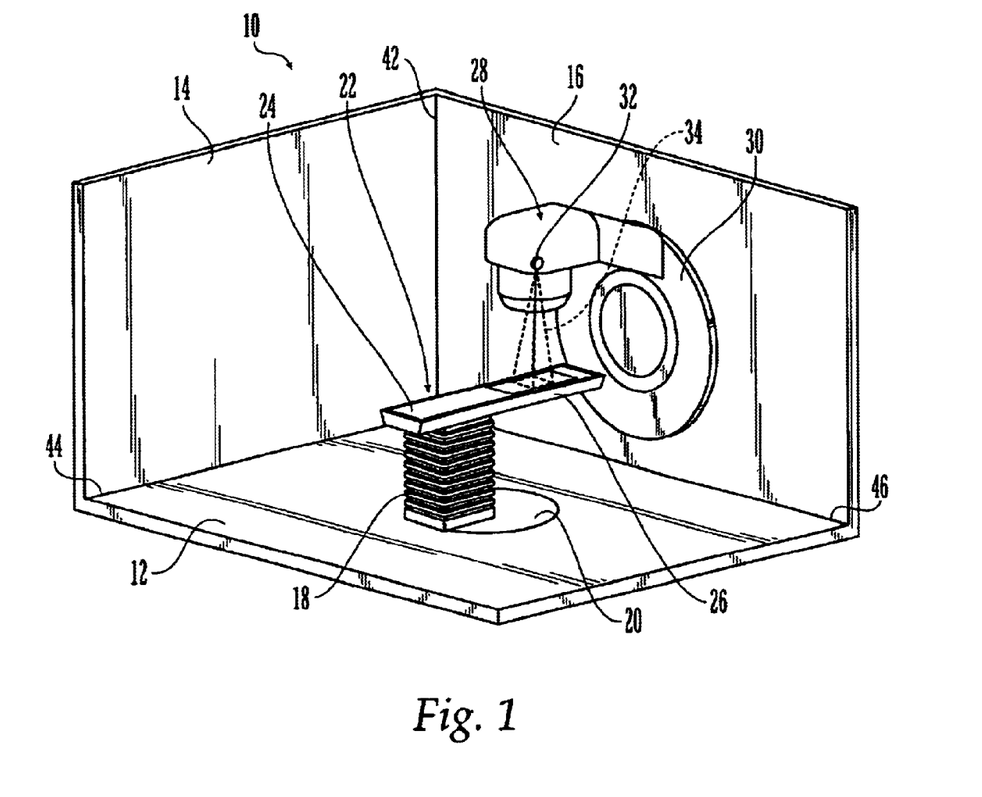
FIG. 1 is a diagrammatic, isometric view of a portion of a treatment room with a patient support table and an accelerator treatment head.

A radiotherapy treatment room 10 is diagrammatically shown in FIG. 1. The treatment room includes a floor 12 and two walls 14, 16. The remaining building structure as well as unrelated equipment have been removed for purposes of clarity. A vertically extending base 18 is mounted to a rotatable floor panel 20. Attached to the top of the rotatable base is a patient support table 22 upon which a patient is placed during radiotherapy and/or imaging treatment.

The support table includes a first section 24 directly attached to the base 18 and a second section 26 which is removably connected to the first table section 24. The above mentioned parent patent application, Ser. No. 10/223,912, describes additional aspects of the table in more detail and that description is incorporated here, in its entirety, by this reference.

The treatment room includes an accelerator treatment head 28 mounted on a rotatable wall panel 30. The treatment head may be rotatable and also may be moved linearly toward and away from the wall 16. This movement, plus the rotational movement of the patient table, allows the treatment head to focus on just about every portion of a patient's body lying on the table. Within the treatment head is a radiation source 32 for emitting radiation within a field generally depicted by the dotted lines 34.

Figure 2:
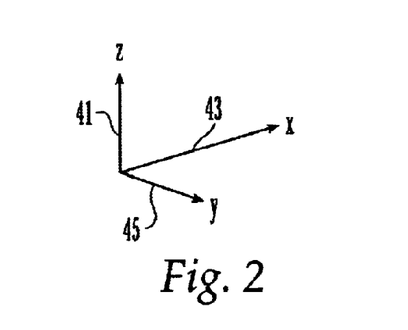
FIG. 2 is an x, y, z coordinate system.

Referring now to FIG. 2, there is shown a traditional x, y, z three dimensional coordinate system 40, which coordinates are mutually perpendicular, where the z coordinate 41 represents a vertical axis and is shown parallel to an intersection 42, FIG. 1, of the walls 14, 16, the x coordinate 43 represents a longitudinal axis of the table and is shown parallel to an intersection 44 of the wall 14 and the floor 12 and they coordinate 45 represents a lateral axis of the table and is shown parallel to an intersection 46 of the wall 16 and the floor 12. The x, y, z coordinate system will be used in this application to help describe various features of the table.

Figure 3:
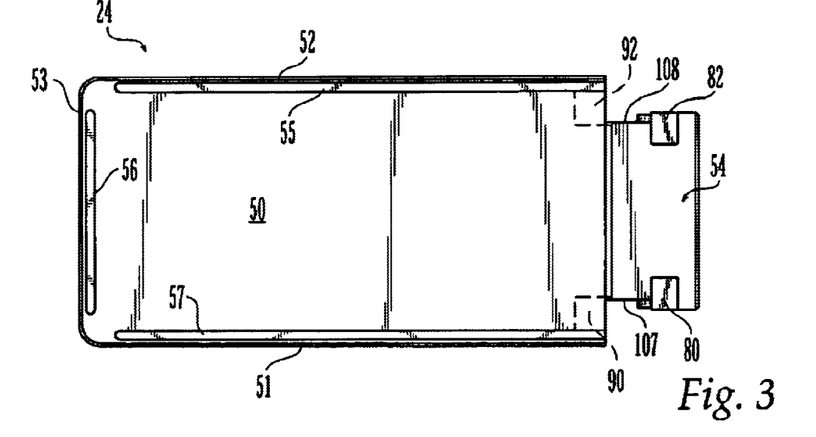
FIG. 3 is a top plan view of a fixed table section of the patient support table.
Figures 4, 5, 7:
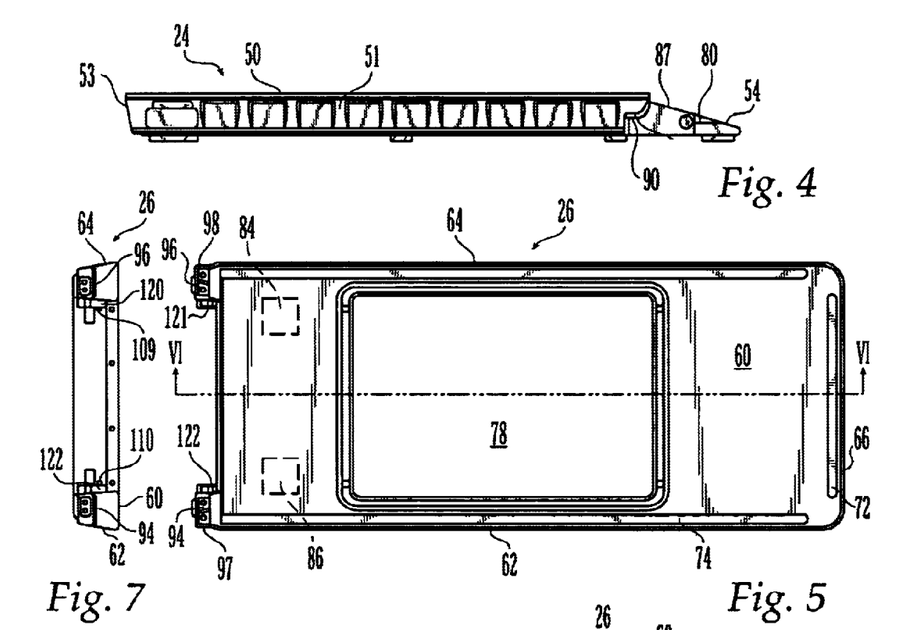
FIG. 4 is a left side elevation view of the fixed table section.
FIG. 5 is a top plan view of a removable table section of the patient support table.
FIG. 7 is a rear elevation view of the removable table section.

The first or fixed table section 24, FIGS. 3 and 4, includes generally a top portion 50, left and right side portions 51, 52, a terminal or rear end portion 53 and a front or connector end portion 54. Formed in the top portion of the first table section are recesses or channels 55, 56, 57, extending longitudinally and laterally, which are used to contain indicia of a measuring system to help in locating the patient's body on the table. By using the term "fixed" in this patent, it is meant that the first table section 24 is fastened or attached to the base 18 and is thereby fixed even though the base itself is rotatable, along with the attached first table section. The second table section 26 is removable and exchangeable with other second table sections but when connected to the first table section, the second table section will also rotate when the base rotates. The first table section is formed of aluminum with plastic laminate for patient comfort.

Figure 6:
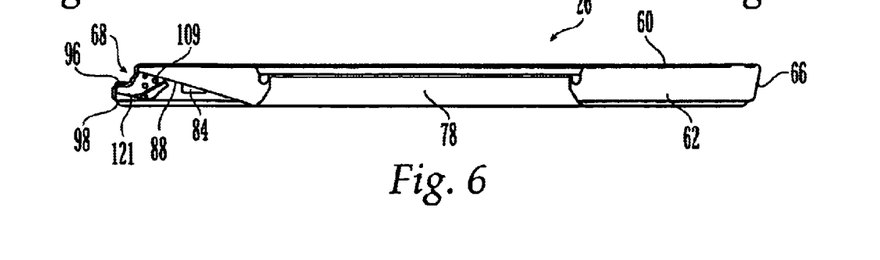
FIG. 6 is a sectional elevation view of the removable table section taken along line 6—6 of FIG. 5.

The second or removable table section 26, FIGS. 5, 6 and 7, includes, generally, a top portion 60, left and right side portions 62, 64, a terminal or front end portion 66 and a connector or rear end portion 68. Formed in the top portion of the second table section are recesses or channels 70, 72, 74 which like the first table section, contains indicia of the measuring system complementing the indicia on the first table section. In the central portion of the second table section is an opening 78. While the opening shown is of a rectangular shape, it may take any of many different shapes and sizes depending upon the patient and the treatment required. The second table section is formed of carbon fiber formed around a foam core.

Referring now to FIGS. 8–11, in addition to FIGS. 3–7, the connector system, or as it sometimes is called, interface mechanism, will be described in detail. The system includes three sets of separate structural surfaces which allow quick and easy connection and disconnection of the second or removable table section with and from the first table section and therefore, allow quick and easy exchange of different removable table sections with the fixed table section. It is very important, however, that each of such removable table sections be located and supported so that positioning is exactly repeatable and that sufficient support is provided for both the removable table section itself and for the patient who reclines on the table sections during treatment.

To provide both support and alignment in the vertical or z-axis, the first table section includes a first pair of upwardly facing horizontal pads 80, 82 positioned on opposite sides of the sloping tongue-like connector end portion 54. The first pair of pads are formed to engage a second pair of downwardly facing, horizontally spaced pads 84, 86 which are formed on the complementary sloping recessed connector end portion 68 of the second table section 26. The sloping surface 87, FIG. 3, of the first table end portion 54 is upward facing while the sloping surface 88, FIG. 5, of the second table end portion 68 if downward facing. All of the exchangeable second table sections include identical connector end portions just like the connector end portion shown in FIGS. 5–7.

Another pair of pads, a third pair 90, 92, are formed at opposite lateral sides of the connector end portion 54 of the first table section 24, downwardly facing, and these engage a fourth pair of pads 94, 96, upwardly facing, formed on straddling legs 97, 98 of the connector end portion 68 of the removable table section 26. The four pairs of pads provide for a stable, secure and robust arrangement for supporting the second table section on the first table section.

A second set of structural surfaces for alignment in the x-axis includes a vertical end surface 100 formed on the first table section where the tongue-like connector end portion 54 meets the remainder of the first table section. This surface engages a rounded edge 101 formed on the connector end portion 68 of the second table section between the legs 97, 98 and the fourth pair of pads 94, 96. A pair of bumper pads 103, 104 are attached to the second table section and they engage two vertical walls 105, 106 on the first table section so as to help align the two table sections.

Figure 12:
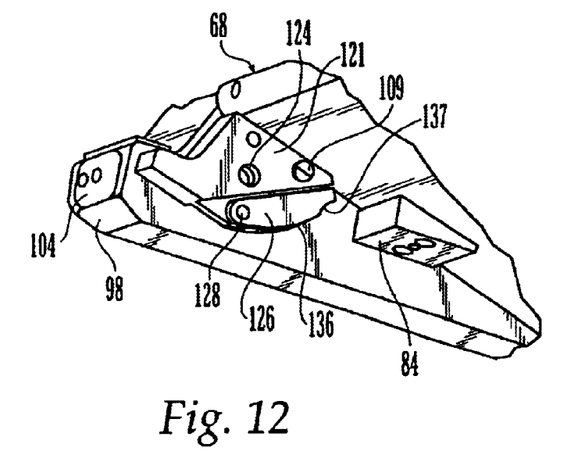
FIG. 12 is an enlarged, upward looking isometric view of a portion of the removable table section.
Figure 13:
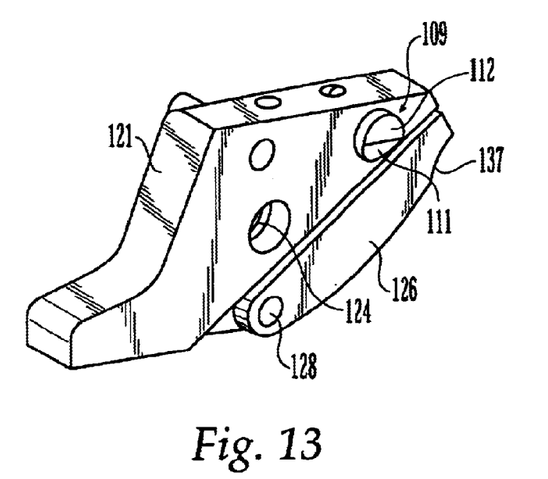
FIG. 13 is an enlarged isometric view of a cam pivoting mechanism.

A third set of structural surfaces for alignment in they-axis direction includes oppositely disposed vertical side surfaces 107, 108 to each side of the tongue-like connector end portion 54 of the first table section 24. These vertical side surfaces are engaged by a pair of oppositely placed beveled pegs 109, 110, FIGS. 11 and 12, connected to the connector end portion 68 of the second table section. Each of the pegs includes a chamfer or beveled lower surface, such as the beveled lower surface 111, FIG. 13, of the peg 109, and a vertical upper surface, such as the vertical upper surface 112 of the peg 109.

Referring to FIG. 9 once again, four bolt pads 113, 114, 115, 116 are shown formed on the underside of the first table section. These allow the first table section to be easily attached to the base 18, FIG. 1. There is also illustrated a reinforcing rib structure, such as the ribs 117, 118 formed in the underside of the first table section.

Figure 8:
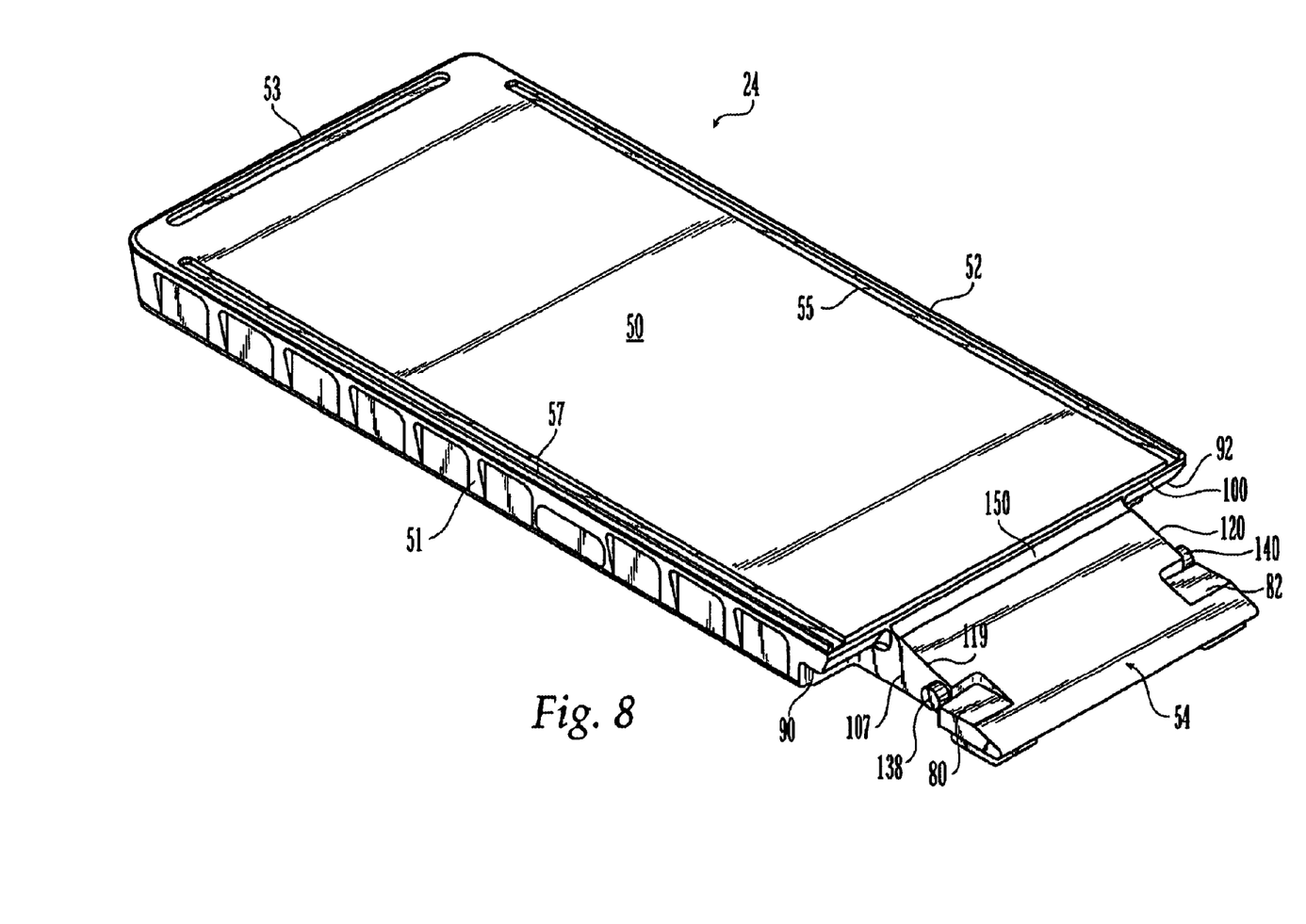
FIG. 8 is a downward looking isometric view of the fixed table section.
Figure 9:
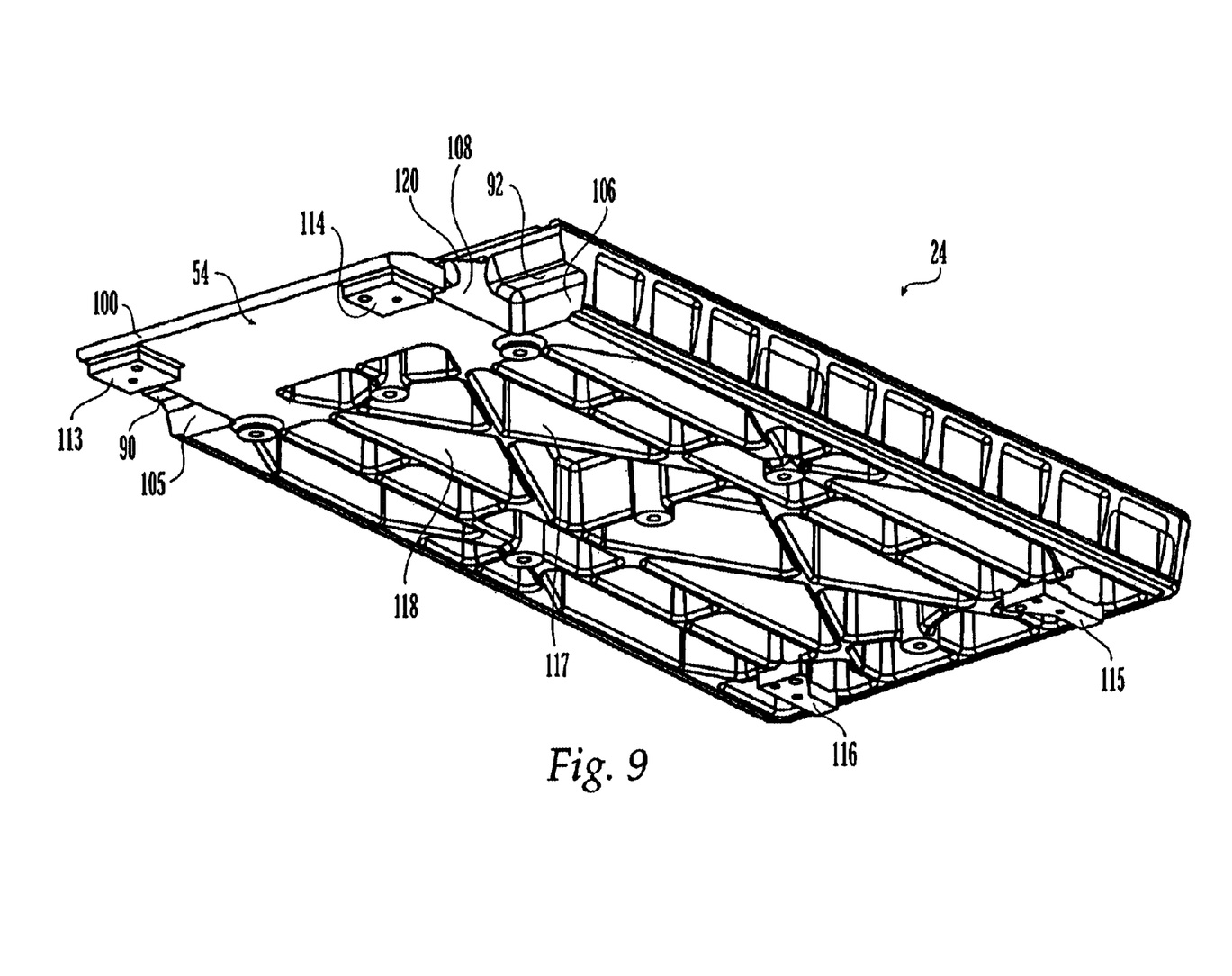
FIG. 9 is an upward looking isometric view of the fixed table section.
Figure 10:
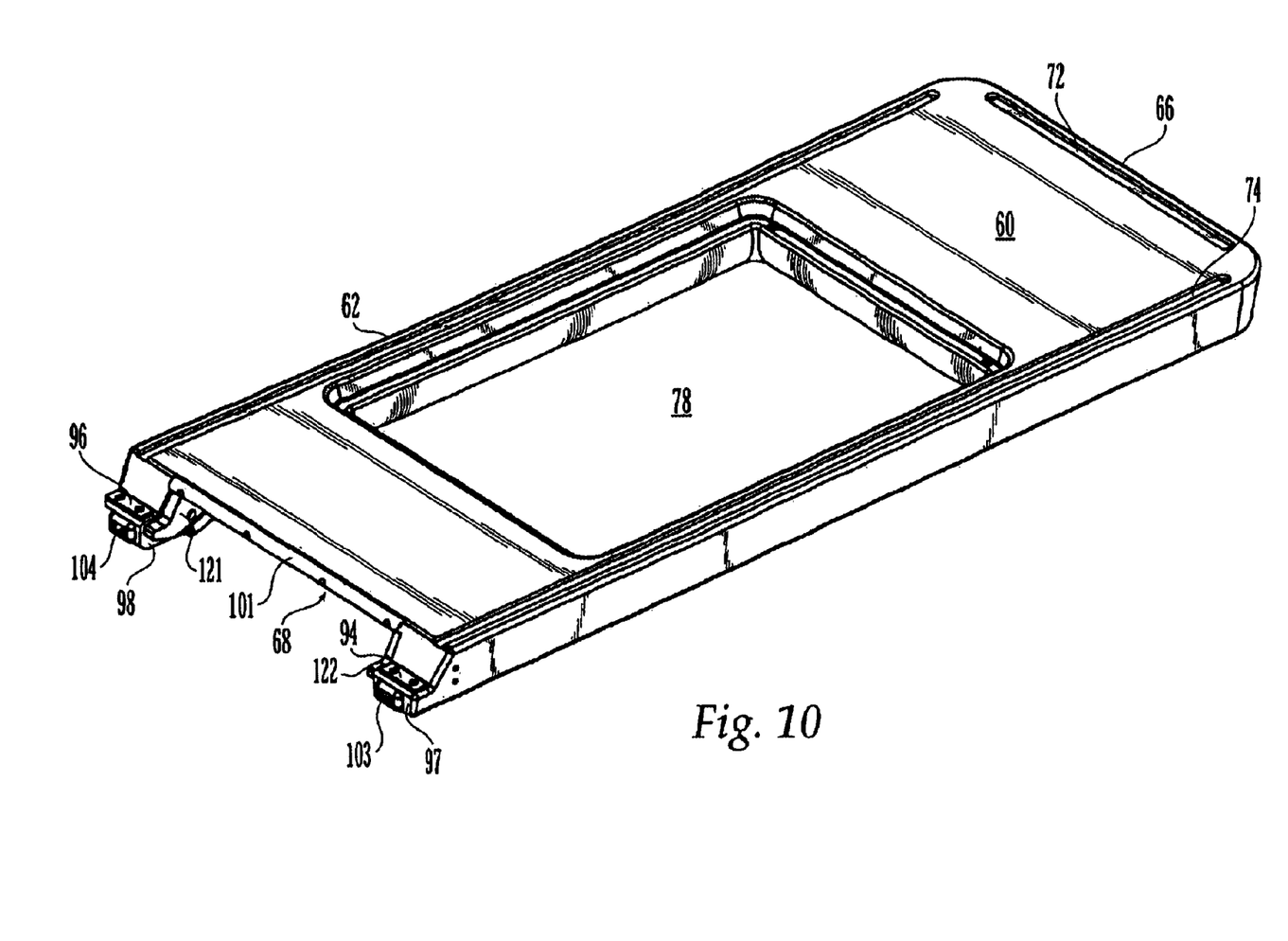
FIG. 10 is a downward looking isometric view of the removable table section.
Figure 11:
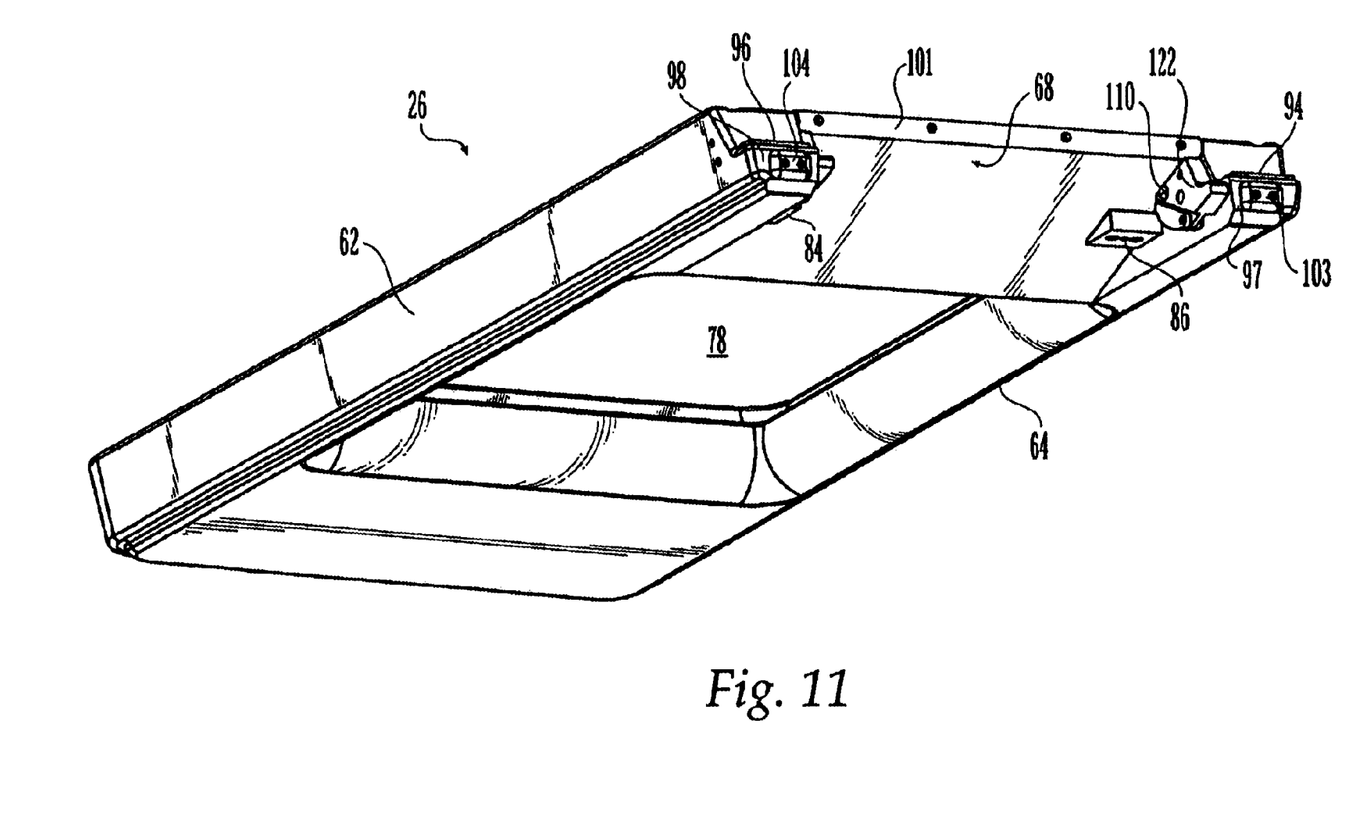
FIG. 11 is an upward looking isometric view of the removable table section.

As will be explained below, when the removable or second table section 26 is brought into contact with the fixed or first table section 24, the beveled lower surfaces of the pegs will engage the upper edges 119, 120, FIGS. 8 and 9, of the vertical side surfaces 107, 108 and induces a force to laterally move the second table section so as to align itself evenly between the pegs 109, 110 so that the pegs slip along the vertical side surfaces 107, 108. Lateral movement of the second table section is thereby blocked by an abutment of one of the pegs against a corresponding one of the vertical side surfaces.

Figure 14:
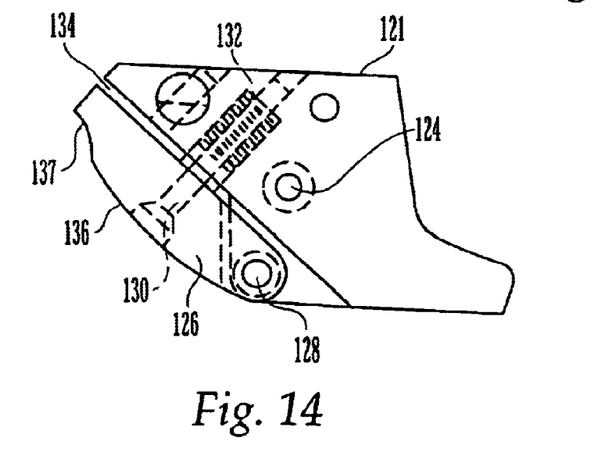
FIG. 14 is a rear elevation view of the cam pivoting mechanism.

During connection of the removable table section and the fixed table section, there are cam mechanisms that support, align and lock the removable table section as it is connected to the fixed table section. The cam mechanisms include a pair of blocks 121, 122, FIGS. 5, 6, 7, 10 and 11, attached to the connector end portion 68 of the removable table section adjacent the fourth pair of pads 94, 96. The blocks are attached to the removable table section by fasteners, such as the fastener 124, FIGS. 12–14, connecting the block 121. The block 121 also supports the beveled peg 109.

The cam mechanisms also include pivotal arms rotatably connected to each of the blocks, such as the pivotal arm 126 connected to the block 121 with a pin 128. Each pivotal arm supports a vertically disposed fastener, such as the fastener 130, which engage springs mounted in the blocks, such as the spring 132. The pivotal arm 126 is mounted in a first position to leave a gap or space 134 between the pivotal arm and the block. The pivotal arm also has a bottom cam follower surface 136. The fastener/spring combination allows the pivotal arm 126 to be biased away from the block should the pivotal arm move to another position toward the block and shorten the gap 134. At the far end of each pivotal arm is a circular recess, such as the recess 137. These circular recesses engage and are cammed by cam rollers 138, 140, FIG. 8, attached to the first table section and projected laterally outwardly. The camming action pivots the arms to a second position toward the blocks so as to close the gaps and induces oppositely directed biasing forces acting to return the pivotal arms to the first position shown in FIGS. 12–14. The block 122, pivotal arm and other elements on the opposite side of the removable table section are a mirror image of the block 121, the pivotal arm 126 and other elements just mentioned.

Figure 15:
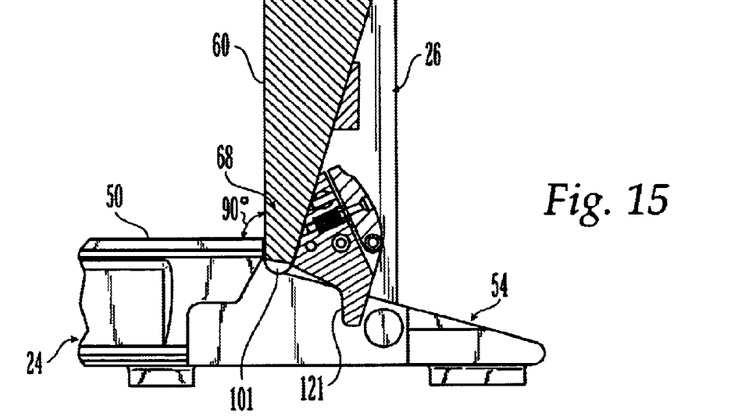
FIG. 15 is a diagrammatic elevation view of portions of the fixed and removable table sections being connected where the table sections are at about ninety degrees to one another.

The operation of connecting the removable or second table section 26 to the fixed or first table section 24 is simple, intuitive and requires minimal effort. To start a connection, the removable table section is held in about a vertical orientation with the top portion 60 of the removable table section at about ninety degrees to the top portion 50 of the fixed table as shown in FIG. 15. The connector end portion 68 of the removable table section is downwardly positioned so that the rounded edge 101 of the removable table section rests in a curved recess 150, FIG. 8, in the connector end portion 54 of the fixed table section. Most of the weight of the removable table section, approximately fifteen to twenty pounds, is supported by the fixed table section. The two legs 97, 98 of the removable table section straddles the tongue-like connector end portion 54 of the fixed table section. This first step aligns the removable table section in the lateral direction along the y-axis. The first step also begins alignment in the longitudinal direction along the z-axis.

Figure 16:
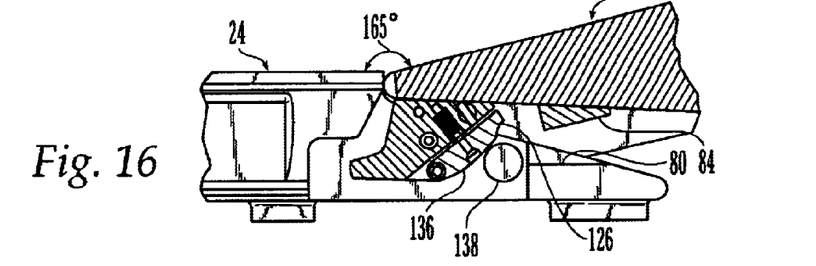
FIG. 16 is a somewhat similar view to that of FIG. 15 but with the movable table section rotated to about one hundred and sixty five degrees.
Figure 17:
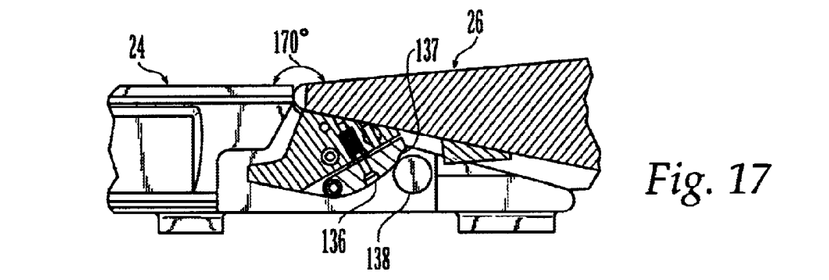
FIG. 17 is a view similar to that of FIG. 16 but with the table sections at about one hundred and seventy degrees.

To complete connection of the two table sections, the removable table section is lowered by pivoting the removable table section about the rounded edge 101. As the removable table section pivots or rotates to about one hundred and sixty degrees, the cam rollers 138, 140 engage the cam follower bottom surfaces of the pivotal arms. This is shown in FIG. 16. The weight of the removable table section creates a component of force along the x-axis, or to the left in FIG. 16, to help keep the two table sections engaged with one another.

Figure 18:
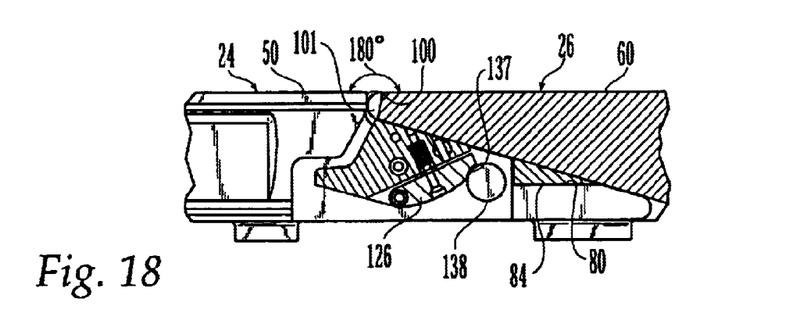
FIG. 18 is a view similar to that of FIGS. 16 and 17 but with the table sections at about one hundred and eighty degrees.

When the removable table section reaches about one hundred and seventy degrees the weight of the removable table section against the cam rollers causes the springs of the cam mechanisms to compress and to narrow the gaps. There is an apparent decrease in the weight of the descending removable table section. There is also an alignment in the lateral direction, along the y-axis, because the beveled surfaces of the beveled pegs come into contact with the upper edges 119, 120 of the vertical side surfaces 107, 108 to shift the lateral position of the removable When the removable table section reaches one hundred eighty degrees as shown in FIG. 18, where the top portion 60 of the removable table section is about level with the top portion 50 of the fixed table section, the cam rollers engage the circular recesses of the pivotal arms which snap into place under the influence of the compressed springs. This causes the leftward bias of the removable table section toward the fixed table section, to ensure engagement and proper seating of the first, second, third and fourth pairs of pads, and the rounded edge 101 of the removable table section with the vertical end surface 100 of the fixed table section.

The engagement of the cam rollers and the circular recesses of the cam follower pivotal arms creates a detent so as to lock the removable table section to the fixed table section by forming an interference fit between the cam rollers and the pivotal arms should there be any horizontal forces acting along the z-axis acting to separate the table sections. The snapping engagement also provides an apparent momentary increase in weight of the removable table section to alert the person connecting the table sections that a lock has been achieved.

Once connected, should someone bump the end of the second table section opposite the connector portion around the terminal end portion 66, the springs of the cam pivoting mechanisms will compress and there will be a misalignment of the removable table section relative to the fixed table section. The alignment of the rounded edge and the vertical end surface will be disrupted with the existing line contact altered to open a gap on the side of the table experiencing the bump or applied load. There will be a pivot of the removable table section around the z-axis. Once the load is removed, the springs will restore the removable table section to the proper aligned location relative to the fixed table section where the rounded edge 101 is again in line contact with the vertical end surface 100.

The removable table section may be disconnected by reversing the steps of the connecting operation. First, the removable table section is pushed inwardly and upwardly to disengage the pivotal arms from the cam rollers. The removable table section is then rotated upwardly toward a ninety degree disposition and lifted away from the fixed table section. Thereafter, another removable table section of different structure may be attached. The removable table sections may come with different sized or shaped cutouts and/or other features that are found to enhance radiotherapy and/or imaging.

The above specification describes in detail the preferred embodiment of the present invention. Other examples, embodiments, modifications and variations will, under both the literal claim language and the doctrine of equivalents, come within the scope of the invention defined by the appended claims. For example, the size and shape of both the first and second table sections may be altered, the size and shape of the connector end portions of the table sections may be modified, the locations of the four pairs of pads or of some of them may be moved and the shape and operation of the cam mechanisms may be varied, and still be considered equivalent structures. Further, the alterations will come within the literal language of the claims. Still other alternatives will also be equivalent as will many new technologies. There is no desire or intention here to limit in any way the application of the doctrine of equivalents nor to limit or restrict the scope of the invention.

What is claimed is:

1. A radiotherapy treatment and imaging patient support table comprising:

a first table section having longitudinal and lateral axes being mounted relative to a floor at a vertical distance above said floor;

a second table section having longitudinal and lateral axes, said second table section being removably attachable to said first table section; and a connector system having three sets of separated structural surfaces, a first portion of each set formed on said first table section and a second portion of each set formed on said second table section, said three sets of separated structural surfaces for accurately and repeatedly enabling alignment and support of said second table section relative to said first table section.

2. The patient support table of claim 1 wherein:

one set of separated structural surfaces of said connector system includes a first pair of horizontally disposed pads formed on said first table section; and a second pair of horizontally disposed pads formed on said second table section.

3. The patient support table of claim 1 wherein:

a second set of structural surfaces of said connector system includes a vertically disposed end surface formed on said first table section; and a horizontally extending edge formed on said second table section.

4. The patient support table of claim 1 wherein:

a third set of structural surfaces of said connector system includes a pair of vertically disposed side surfaces formed on one of said table sections; and a pair of laterally extending projections formed on the other of said table sections.

5. The patient support table of claim 1 wherein:

one set of structural surfaces of said connector system includes a first pair of horizontally disposed pads formed on said first table section and a second pair of horizontally disposed pads formed on said second table section; and a second set of structural surfaces of said connector system includes a vertically disposed end surface formed on said first table section and a horizontally extending edge formed on said second table section.

6. The patient support table of claim 1 wherein:

one set of separated structural surfaces of said connector system includes a first pair of horizontally disposed pads formed on said first table section and a second pair of horizontally disposed pads formed on said second table section; and another set of structural surfaces of said connector system includes a pair of vertically disposed side surfaces formed on said first table section and a pair of laterally extending projections formed on said second table section.

7. The patient support table of claim 1 wherein:

one set of structural surfaces of said connector system includes a vertically disposed end surface formed on said first table section and a horizontally extending edge formed on said second table section; and another set of structural surfaces of said connector system includes a pair of vertically disposed side surfaces formed on said first table section and a pair of laterally extending projections formed on said second table section.

8. The patient support table of claim 1 wherein:

one set of separated structural surfaces of said connector system includes a first pair of horizontally disposed pads formed on said first table section and a second pair of horizontally disposed pads formed on said second table section;

a second set of structural surfaces of said connector system includes a vertically disposed end surface formed on said first table section and a horizontally extending edge formed on said second table section; and a third set of structural surfaces of said connector system includes a pair of vertically disposed side surfaces formed on one of said table sections and a pair of laterally extending projections formed on the other of said second table sections.

9. The patient support table of claim 1 wherein:

one set of structural surfaces of said connector system includes a vertically disposed end surface formed on said first table section and a horizontally extending edge formed on said second table section;

another set of structural surfaces of said connector system includes a first pair of horizontally disposed pads formed on said first table section and a second pair of horizontally disposed pads formed on said second table section; and a further set of structural surfaces of said connector system includes a vertically disposed end surface formed on said first table section and a horizontally extending edge formed on said second table section.

10. The patient support table of claim 8 wherein:

said third set of structural surfaces of said connector system includes a vertically disposed end surface formed on said first table section and a horizontally extending edge formed on said second table section.

11. The patient support table of claim 2 wherein:

said first pair of horizontally disposed pads on said first table section and said second pair of horizontally disposed pads on said second table section are located to engage one another when said second table section is fully connected to said first table section.

12. The patient support table of claim 11 wherein:

said one set of structural surfaces of said connector system includes a third pair of horizontally disposed pads formed on said first table section; and a fourth pair of horizontally disposed pads formed on said second table section.

13. The patient support table of claim 12 wherein:

said first and said third pairs of horizontally disposed pads on said first table section and said second and said fourth pairs of horizontally disposed pads on said second table section are located such that said first and said second pairs of pads engage one another and said third and said fourth pairs of pads engage one another when said second table section is fully connected to said first table section.

14. The patient support table of claim 12 wherein:

said first pair of pads is longitudinally spaced from said third pair of pads.

15. The patient support table of claim 14 wherein:
said first pair of pads is vertically spaced from said third pair of pads.

16. The patient support table of claim 12 wherein:
said first pair of pads is vertically spaced from said third pair of pads.

17. The patient support table of claim 3 wherein:
said horizontally extending edge of said second table section is rounded.

18. The patient support table of claim 5 wherein:
said horizontally extending edge of said second table section is rounded.

19. The patient support table of claim 8 wherein:
said horizontally extending edge of said second table section is rounded.

20. The patient support table of claim 4 wherein:
said projections are disposed to align said second table section laterally relative to said first table section.

21. The patient support table of claim 8 wherein:
said projections are disposed to align said second table section laterally relative to said first table section.

22. The patient support table of claim 20 wherein:
said projections each include a chamfer to adjust the lateral position of said second table section relative to said first table section as said table section is connected to said first table section.

23. The patient support table of claim 21 wherein:
said projections each include a chamfer to adjust the lateral position of said second table section relative to said first table section as said table section is connected to said first table section.

24. The patient support table of claim 1 including:
a detent mounted to said support table for restraining said second table section relative to said first table section.

25. The patient support table of claim 24 wherein:
said detent includes a pivotal cam follower.

26. The patient support table of claim 25 wherein:
said cam follower is biased to a first position, and during engagement of said second table section to said first table section, said cam follower moves from said first position to a second position before returning to said first position.

27. The patient support table of claim 26 wherein:
said detent includes a roller cam.

28. The patient support table of claim 24 wherein:
said detent includes a roller cam.

29. The patient support table of claim 1 wherein:
said first table section includes a longitudinally extending tongue-like portion.

30. The patient support table of claim 29 wherein:
said second table section includes a pair of legs for straddling said tongue-like portion of said first table section.

31. The patient support table of claim 30 wherein:
said tongue-like portion of said first table section includes a sloping surface.

32. The patient support table of claim 31 wherein:
said second table section includes a sloping surface.

33. The patient support table of claim 32 wherein:
said sloping surface of said tongue-like portion of said first table section is disposed on top of said tongue-like portion; and said sloping surface of said second table section is downwardly facing.

34. The patient support table of claim 8 including:
a detent mounted to said support table for restraining said second table section relative to said first table section.

35. The patient support table of claim 34 wherein:
said detent includes a pivotal cam follower;

said cam follower is biased to a first position, and during engagement of said second table section to said first table section, said cam follower moves from said first position to a second position before returning to said first position; and said detent includes a roller cam.

36. The patient support table of claim 34 wherein:
said first table section includes a longitudinally extending tongue-like portion; and said second table section includes a pair of legs for straddling said tongue-like portion of said first table section.

37. The patient support table of claim 36 wherein:
said tongue-like portion of said first table section includes a sloping surface; and said second table section includes a sloping surface.

38. The patient support table of claim 37 wherein:
said sloping surface of said tongue-like portion of said first table section is disposed on top of said tongue-like portion; and said sloping surface of said second table section is downwardly facing.

39. The patient support table of claim 36 wherein:
said detent includes a pivotal cam follower;

said cam follower is biased to a first position, and during engagement of said second table section to said first table section, said cam follower moves from said first position to a second position before returning to said first position; and said detent includes a roller cam.

40. The patient support table of claim 39 wherein:
said tongue-like portion of said first table section includes a sloping surface;

said second table section includes a sloping surface;

said sloping surface of said tongue-like portion of said first table section is disposed on top of said tongue-like portion; and said sloping surface of said second table section is downwardly facing.

* * * * *